(12) United States Patent
Lorber et al.

(10) Patent No.: US 7,933,719 B2
(45) Date of Patent: *Apr. 26, 2011

(54) METHODS AND APPARATUS FOR DIAGNOSTIC ASSESSMENT BASED ON AMOUNTS OF BIOGENIC AMINES

(75) Inventors: Avraham Lorber, Metar (IL); Zeev Karpas, Omer (IL)

(73) Assignee: 3 Q B D Ltd. (IL)

( * ) Notice: Subject to any disclaimer, the term of this patent is extended or adjusted under 35 U.S.C. 154(b) by 737 days.

This patent is subject to a terminal disclaimer.

(21) Appl. No.: 11/007,365

(22) Filed: Dec. 8, 2004

(65) Prior Publication Data

US 2005/0095720 A1    May 5, 2005

Related U.S. Application Data

(63) Continuation of application No. 10/079,624, filed on Feb. 20, 2002, now abandoned, which is a continuation-in-part of application No. 09/813,523, filed on Mar. 21, 2001, now Pat. No. 7,056,745.

(30) Foreign Application Priority Data

Feb. 1, 2001  (IL) ........................................ 141233
Nov. 22, 2001 (IL) ........................................ 146698

(51) Int. Cl.
G01N 33/48   (2006.01)
G01N 31/00   (2006.01)
C12Q 1/02    (2006.01)
C12M 1/00    (2006.01)
G06G 7/58    (2006.01)

(52) U.S. Cl. ........... 702/19; 435/29; 435/283.1; 702/22; 703/12

(58) Field of Classification Search ........................ None
See application file for complete search history.

(56) References Cited

U.S. PATENT DOCUMENTS

| 4,001,213 | A |   | 1/1977 | Hershman et al. |
| 4,080,488 | A |   | 3/1978 | Chen et al. |
| 5,109,691 | A |   | 5/1992 | Corrigan et al. |
| 5,447,556 | A | * | 9/1995 | Pleil et al. ........................ 95/87 |
| 5,856,616 | A |   | 1/1999 | Maswadeh et al. |
| 6,387,329 | B1 |  | 5/2002 | Lewis et al. |
| 6,428,748 | B1 |  | 8/2002 | Wallach |

FOREIGN PATENT DOCUMENTS

| WO | WO-00/20852 A1 | 4/2000 |
| WO | 02/061425 A2 | 8/2002 |

OTHER PUBLICATIONS

Chen et al. "Amine Content of Vaginal Fluif from Treated and Untreated Patients with Nonspecific Vaginitis" J. Clin. Invest. (1979) pp. 828-835.*
Lawrence, P.J. et al. "Spectrophotometric quantitation of vaginal fluid trimethylamine and comparative performance of olfactory trimethylamine (KOH whiff test) detection and a new colorimetric chemical test,"Clinical Chemistry, vol. 45 No. 6 Part 2, Jun. 1999, p. A162 XP001118327 51st Annual Meeting of the American Association of Clinical Chemistry, New Orleans, LA, USA, Jul. 25-29, 1999 IISN: 0009-9147 abstract.
Suh, Ja Won, et al. "Urinary Polymine Evaluation for Effective Diagnonosis of Various Cancers" J. Chromatog B, V of 688 (1997) pp. 179-186.
Chen, K.C.S., et al. "Biochemical Diagnosis of Vaginitis: Deternination of Diarrines in Vaginal Fluid" J. Infect. Dis vol. 145 (1982) pp. 337-345.
Karpas, Z, "Ion Mobility Spectromerty of Allohatic and Aromatic Amines" Chem, Vo. 61, (1989), pp. 684-689.
Baumbach, J. I., et al, , Ion Mobility Spectrometry: Arriving on Site and Moving Beyond a Low Profile, Appl. Spectrose, vol. 53, (1999), pp. 338A-355 A.
Karpas et al., "The Structure of Protonated Diamines and Polymaines," Struct. Chem., vol. 5, (1994) pp. 135-140.
International Search Report, PCT/IL2010/000483, dated Nov. 5, 2010.
Chaim Walter et al: "New technology for diagnosis of bacterial vaginosis," European Journal of Obstetrics, Gynecology, and Reproductive Biology Nov. 10, 2003 LNKD-PUBMED:14557018, vol. 111, No. 1, Nov. 10, 2003, pp. 83-87, XP002605532.
Karpas Z et al: "Novel application for ion mobility spectrometry: Diagnosing vaginal infections through measurement of biogenic amines" ANALYTICA CHIM1CA ACTA 20021209 NL LNKDD01: 10.1016/S0003-2670(02)01007-3, vol. 474, No. 1-2, Dec. 9, 2002, pp. 115-123, XP002605533.

* cited by examiner

*Primary Examiner* — Eric S Dejong
(74) *Attorney, Agent, or Firm* — Lerner, David, Littenberg, Krumholz & Mentlik, LLP

(57) ABSTRACT

Diagnostic method, based on the amounts of biogenic amines that are contained in a body fluid or other sample. A number of measured parameters related to the desired diagnostic information are derived from the amounts. For each diagnostic information desired, an input consisting of the identification of the diagnostic information is provided. The input is compared to the measured parameters and a diagnostic response is derived from the comparison. The measured parameters may be derived from the amounts of the biogenic amines according to a program stored in a memory. The detection of the less volatile amines and their separation from the more volatile ones may advantageously be enhanced by successively adding a base and an acid, in either possible succession, to the sample and analyzing the vapors emitted by the sample under heating.

24 Claims, 13 Drawing Sheets

METHODS AND APPARATUS FOR DIAGNOSTIC ASSESSMENT BASED ON AMOUNTS OF BIOGENIC AMINES

CROSS-REFERENCE TO RELATED APPLICATIONS

The present application is a continuation of U.S. application Ser. No. 10/079,624, filed Feb. 20, 2002 (abandoned), which is a continuation-in-part of U.S. application Ser. No. 09/813,523, filed on Mar. 21, 2001, which claims priority from Israeli Appln. No. 141233, filed Feb. 1, 2001; and a continuation-in-part of International Application No. PCT/IL02/00087 filed Jan. 31, 2002, published Aug. 8, 2002, which claims priority from Israeli application 141233 filed Feb. 1, 2001 and Israeli application 146698 filed Nov. 22, 2001, all of which are incorporated herein by reference.

BACKGROUND OF THE INVENTION

The invention relates to a method for diagnosing certain pathological conditions, particularly vaginal disorders, by determining biogenic amines in samples of body fluids or other samples and distinguishing between more volatile and the less volatile amine species. The invention also includes selectively enhancing the emanation of the less volatile species and performing a partial separation between the more volatile and the less volatile species. The invention also relates to an apparatus for automatically providing diagnoses of certain pathological conditions and/or relevant diagnostic information.

It is known in the art that the presence of biogenic amines in human body fluids may reveal or suggest pathological conditions and dysfunctions. For example, elevated levels of certain biogenic amines in urine may indicate the presence or the likelihood of the presence of a cancer (there are many papers dealing with this—see, for instance, Suh, J W, Lee, S H, Chung, B C, Park, J, *Urinary Polyamine Evaluation for Effective Diagnosis of Various Cancers*, Journal of Chromatography B, 1997, Vol. 688, Iss 2, pp. 179-186). Several of the types of vaginal diseases may be expressed in elevated levels of biogenic amines in vaginal discharge and fluids (see, for instance, C. S. Chen, R. Amsel, D. A. Eschenbach and K. K. Holmes, *Biochemical diagnosis of vaginitis: determination of diamines in vaginal fluid*, J. Infectious Disease 145 (1982), pp. 337-345).

Body fluids may include e.g. urine, blood, serum, saliva, vaginal discharge and fluids, etc. Further, samples in which the presence of biogenic amines may be determined may not be fluids, but, e.g., skin and tissues, swipe samples, etc. Even direct sniffing of skin or breath exhaled by a subject may provide information in this respect. This should be understood whenever body fluids are mentioned in this application.

Chemical changes in the living system or degradation processes of cells after death are accompanied with formation of molecular byproducts. These processes include the breaking down of peptides and DNA strands to smaller components, and changes in the building blocks, amino acids, leading to the formation of amines. Not only amino compounds are produced, but other, smaller molecules, such as aldehydes and alcohols are also formed. One of the processes of particular interest is the breakdown of amino acids and the production of amines, diamines and polyamines. For example, decarboxylation of histidine, ornithine, lysine, produces histamine, putrescine and cadaverine, respectively.

Several analytical methods have been proposed for the analysis of biogenic amines. Most of these are laboratory methods that require expensive equipment, extensive sample preparation and the skills of a trained analytical chemist or technician. Among these are high performance liquid chromatography (HPLC), or gas chromatography after derivatization of the samples. Biosensors may also be used, as well as various spectrometric techniques. Solid state sensors have also been proposed, but generally lack specificity.

Ion Mobility Spectrometry (also, briefly, IMS) is a known analytical method and its application for the determination of aliphatic and aromatic amines has been suggested: see, for instance, Z. Karpas, *Ion Mobility Spectrometry of Aliphatic and Aromatic Amines*, Anal. Chem. 61 (1989), 684. An apparatus for carrying out this method—the Ion Mobility Spectrometer (IMS)—is used primarily for detection, identification and monitoring of trace amounts of gases and vapors. It is particularly suitable for detection of compounds that have high proton affinity and form stable positive ions, or for compounds that have a high electronegativity and readily form stable negative ions. IMS is fully discussed in J. I. Baumbach and G. A. Eiceman, Appl. Spectrosc. 1999, vol. 53, pp. 338A-355A. However, any device that may be used for determining or measuring the mobility of ions may be used for carrying out the invention, and therefore any reference to IMS in this description and claims should not be construed as a limitation, but should be construed any including instrument for determining or measuring the mobility of ions.

The knowledge of the prior art as to the importance of biogenic amines for the possible detection of pathological conditions and as to the analysis of biogenic amines, including the use of IMS, has failed so far to provide a simple and reliable method for the diagnosis of vaginal disorders, particularly, though not exclusively, bacterial vaginosis that affects a large number of women. The provision of such a diagnostic method would constitute a valuable contribution to the medical art. However, such a method is not available: the detection of biogenic amines in vaginal fluids is known to suggest the presence of a pathological condition, but it does not provide specific and reliable information and merely suggests to the specialized physician the desirability of carrying out whatever tests and examinations may finally lead to a diagnosis.

Samples collected from vegetation, clinical or biological media (the samples) contain biogenic amines that arise from degradation of amino acids through enzymatic and microbial processes. The types of biogenic amines and their quantities are indicative of the progress of said degradation processes, and can thus serve as a measure for food spoilage or the existence and extent of pathological conditions.

Some analytical methods for measuring biogenic amines, such as gas chromatography (GC) or ion mobility spectrometry (IMS), are based on determining their amount in the gas phase. However, while some of these biogenic amines are highly volatile, like trimethylamine (TMA), most have very low vapor pressures at room temperature, and are hardly present in the gas phase. Another reason for this is that biogenic amines may be present in the samples as salts, such as a hydrochloride form, and not present in the more volatile free-base structure. In such cases, their vapor pressure may be very low, and their detection and quantification by gas phase techniques may be very difficult.

One common practice to overcome such difficulties is to dissociate the salts and produce the free-bases by addition of an alkaline solution. For example, in carrying out the Amsel test for detection of bacterial vaginosis (a common vaginal infection), the physician adds a drop of 10% KOH solution to a swab collected from the vaginal fluid and tries to detect the presence of volatile amines by sniffing the sample (the so-called "whiff test").

Further, the present knowledge does not provide the practicing physician with an apparatus for the quick diagnosis of bacterial vaginosis and other pathological conditions, by a simple and direct way and without the application of knowledge and technology that are typical of different branches of science and are not found together in any physician, no matter how competent and dedicated. It would be extremely valuable to provide an instrument and method whereby the average physician could obtain from bodily fluids, quickly and in a reliable way, a diagnostic indication of specific diseases and/or pathological conditions, even though such a diagnostic indication may not be final and conclusive and may require, whether positive or negative, verification and integration.

It is therefore a purpose of this invention to provide method for the diagnosis of vaginal disorders, particularly, though not exclusively, bacterial vaginosis.

It is another purpose to provide a method for carrying out such diagnosis automatically and in real time.

It is a further purpose to provide, automatically and in real time, information of fundamental value in the diagnosis of a variety of pathological conditions.

It is a still further purpose to overcome the problems arising in the detection of less volatile or semi-volatile amines, not only in clinical samples, but also in any vegetal or biological medium.

It is a still further purpose to selectively enhance the detection of less volatile or semi-volatile biogenic amines.

It is a still further purpose of this invention to permit to separate, at least partially, the more volatile from the less volatile amines.

It is a still further purpose to provide an apparatus for the quick diagnosis of bacterial vaginosis and other pathological conditions.

It is a still further purpose to provide a portable instrument that is capable of carrying out the spectrometry of bodily fluids and automatically derive from said spectrometry significant diagnostic indications.

It is a still further purpose to provide such an instrument that can be directed to provide diagnostic indications for specific diseases and/or pathological conditions.

It is a still further purpose to provide such an instrument that consists of the combination of components known in the art and readily available.

It is a still further purpose to provide such an instrument that can be widely used by physicians and medical institutions and is not excessively expensive.

It is a still further purpose to provide such an instrument which can be used, with the due precautions and warnings, by persons other than physicians and even by the patients themselves.

It is a still further purpose to provide such an instrument which can be used for purposes that are not diagnostic purposes, but are relevant to the public health, for instance, the control of the condition of food, such as, but not exclusively, the freshness of meat, fish and their products, as well as seafood.

It is a still further purpose to provide such an instrument that permits instant examination of tissues removed during an operation, or medical procedure, as an indication for malignant tissues.

Other purposes and advantages of the invention will appear as the description proceeds.

SUMMARY OF THE INVENTION

The invention provides a method for the diagnosis of vaginal diseases, particularly bacterial vaginosis, which comprises determining the presence of trimethylamine (hereinafter, TMA) ions in vaginal fluid. According to the method, preferably, the total amount of amine ions is measured, and if the number of TMA ions is 40% or more the total number of amine ions, the presence of bacterial vaginosis is recognized, while if the number of TMA ions is 20% or less, the absence of bacterial vaginosis is recognized. The ratio of the number of ions of a given amine to the total number of amine ions could also be called "equivalent ratio" or "concentration of the given amine by equivalents".

Levels of putrescine and cadaverine are also measured, according to the invention, and if the number of their ions is above 10% of the total number of amines ions, various pathological conditions are suspected, as will be detailed hereinafter.

A way of carrying out the method of the invention is the following:

(1) the measurement of the presence of volatile amine compounds, including tertiary amines like trimethylamine (TMA) and other amines, diamines like putrescine and cadaverine as well as polyamines like spermidine and spermine by the appearance of ions derived from these substances in the ion mobility measurement.

(2) samples of the body (e.g. vaginal) fluid, either on a sterile applicator or by any other method, are placed in the sample holder or introduction system, and vapors emanating from said sample are ionized, forming ions that are specific for the said substances.

(3) enhancement of vapor emanation may be carried out by the addition of an appropriate chemical reagent, that transforms the complex amine compounds, like salts and acidic forms, to more volatile forms. For example, this reagent can be comprised of an alkaline solution, like KOH, NaOH and/or ammonia.

(4) a direct device for sampling vapors emanating from the vaginal area may be used to transfer said vapors directly to the measuring device.

(5) control of the ion chemistry by addition of a reagent substance, comprising a volatile amine with proton affinity above that of most common interfering compounds but below that of said amine compounds, may be used to improve the ability to detect the presence of said amine substances.

The invention also provides a diagnostic apparatus which comprises:

I—an apparatus for measuring the mobility of ions, e.g. an Ion Mobility Spectrometer (IMS) for the determination of the amounts of biogenic amines contained in a body fluid or other sample;

II—a first elaborator means for deriving from said amounts a number of parameters related to the diagnostic information that is desired in any specific case;

III—buffer memory means for storing the parameters derived from the aforesaid determination of the amounts of biogenic amines—hereinafter, "the measured parameters";

IV—a second elaborator means for deriving, from the input consisting of the identification of the diagnostic information desired and of the measured parameters, a diagnostic response.

V—memory means for storing programs controlling the operations of the first and second eleborator and for memorizing comparative parameters related to said diagnostic information;

The first and second elaborator means may consist of computer means and may be comprised together in a single computer. However, use may be made in certain cases of tables—LUTs—in place of computers or parts of computers.

The diagnostic response may be in some cases the statement of the presence of a disease or a pathological condition, or the statement that such a disease or pathological condition is suspected and its presence must be verified, or similar statements relative to the absence of a disease or pathological condition, or the statement that no conclusion can be drawn from the measured parameters or that no conclusion can be drawn for other reasons.

A similar response can be obtained from the apparatus if it is used not for diagnostic purposes, but for checking food.

The Ion Mobility Spectrometer will provide a spectrum of the biogenic amines, including peaks for certain amines. Ion mobility measurements by other methods would likewise provide a quantitative value for the presence of certain amines. The first elaborator will be so programmed that it will firstly select the amines that are relevant for the specific response that should be given. Based on said selection, the elaborator will decide whether the measured parameters should comprise the height of the peaks of the relevant amines or areas of the spectrum about said peaks, within certain predetermined ranges, or other parameters which will be defined by the first elaborator program. Similar parameters, of course, may be determined, if needed, for the amines that are not related to the specific response to be given. Alternatively, the measured parameters may be constituted by ratios between heights of peaks or areas of the spectrum. The measured parameters need not be memorized permanently, and therefore are stored in a buffer memory, but if required, may be transferred from the buffer memory to the permanent one.

The permanent memory of the apparatus will contain comparative parameters for each response possibly desired. Comparative parameters will be easily provided by determining the spectra of bodily fluids of different subjects that are free of the disease or pathological condition to which said response refers, determining the measured parameters of said subjects, and averaging said measured parameters of a sufficient number of subjects. Of course, the average may not be a simple mathematical average, but the measured parameters of each subject may be weighted by coefficients which take into account the specific characteristics of each subject, including any characteristics that are relevant to the specific response in question. For instance, if the presence of prostate cancer is to be determined, the age of the subjects tested will be an extremely relevant characteristic. Of course, in such a case, different comparative parameters may be memorized for different ages of subjects. The physicians that will program the first elaborator will know what characteristics are relevant and will know how to determine the comparative parameters for each disease or pathological condition.

The second elaborator will be programmed to determine from the differences between the measured parameters and the comparative parameters the likelihood of the presence of the disease or pathological condition being considered. The program will comprise determining the difference between said measured and said comparative parameters, defined in any suitable way, for instance, as a ratio of numerical values or as a value derived from a predetermined formula relating to the specific response desired; and deriving, from another predetermined formula or from the response to a number of typical questions, an index of the probability of the presence of the disease or pathological condition in question, or a response that is more complex than the mere indication of an index.

In its broader aspects, and beyond the specific aspect of diagnosing vaginal diseases, particularly bacterial vaginosis and related pathological conditions, the method of the invention applies to any situation in which the determination of the amounts of biogenic amines in any sample, whether derived from the human body or having any other origin or nature, may provide valuable information for any purpose, including but not exclusive to the diagnosis of pathological conditions. For instance, said information may be relevant to the use of a biological material as food or to any other use. Therefore, in a broader aspect, the method of the invention comprises the steps of:

a) determining the amounts of biogenic amines contained in a biological sample;
b) deriving from said amounts a number of measured parameters related to the desired information;
c) providing, for each information desired, an input consisting of the identification of said information;
d) comparing said input to said measured parameters; and
e) deriving from said comparison a response.

When the method is applied to diagnostic purposes, the sample is generally a body fluid, the desired information has a diagnostic relevance and the response derived is a diagnostic response. Since this is a most frequent case, reference will be made to it hereinafter, for purposes of description and not of limitation.

Step a) is carried out for each diagnostic operation and its results may be stored in a buffer memory. Step b) may be carried out according to a program stored in a buffer or permanent memory. Step c) may be carried out distinctly for each diagnostic operation, or may be have been carried out previously for a number of expected such operations and the results may be stored in a buffer or permanent memory. Step e) will be carried out according to a stored program that will associate a diagnostic response to results of the comparison of the aforesaid input to said measured parameter, for each of the expected diagnostic operations; but such a program may be derived, for particular cases, if it is not stored. It will be obvious that, if the invention is carried out for checking food, the diagnostic response will only consist in classifying food according to its edibility, e.g. as safe, doubtful, or spoiled.

A preferred embodiment of the method of the invention comprises successively adding a base and an acid to the sample, the amines content of which is to be determined, and analyzing the vapors emitted by the sample under heating, so as to enhance the detection of the less volatile or semi-volatile amines (e.g. putrescine and cadaverine). Preferably, the vapors emitted at room temperature are analyzed as well, to enhance the detection of the more volatile amines (e.g. TMA).

The order of the addition of base and acid is not essential: the base may be added firstly and the acid later, or vice versa. Preferably, the base is a strong alkaline solution, such as, e.g. a solution of KOH or NaOH, and the acid is preferably a diluted mineral acid, such as e.g. a 10% solution of nitric acid.

In a particular form, the method comprises the steps of:
a) providing a sample the amines content of which is to be determined;
b) adding an acid to the sample;
c) adding a base to the sample;
d) subsequently, collecting the vapors emanating from the sample at room temperature and determining their content of amines;
e) heating the sample; and
f) collecting the vapors emanating from the samples upon heating and determining their content of amines.

As hereinbefore stated, step c may precede step b, and in general the order of the steps may be changed as desired.

If the acid is added before the base, it should be sufficient to bring the pH, which will then generally be about 7, down to about 1-2. Actually, for most samples, a drop of 10% nitric acid will suffice. The amount of base added later should be sufficient to raise the pH to about 14, in spite of the previous addition of the acid. If the base is added first, its amount should be sufficient to raise the pH to about 14. The subsequent addition of acid should be in an amount that would have been sufficient, if added before the base, to bring the pH from 7 down to 1-2. Such subsequent addition of acid will have practically no effect on the pH, which will remain at about 14. Therefore, no matter what the succession of the additions of acid and base, the final pH of the sample should be about 14. As an indication of the amount of base involved, if 0.1 ml of a mixture of TMA, putrescine and cadaverine is the amine component of the sample, 0.3 mL of 4N KOH could be used. The aforesaid pH indications, however, are illustrative but not binding, and the amounts of acid and base can be adjusted according to cases. It can always be checked by preparing a test sample including a known mixture of the volatile and semi-volatile amines that are to be detected, and verifying that the amounts of acid and base that are intended to be used will cause the emanation of vapors, the ion mobility spectra of which are in agreement with the known composition of said mixture.

Additional steps, particularly intermediate ones, such as a heating, or a measurement of the vapors at room temperature, between steps b and c, may be added to the form of the method defined hereinbefore, for achieving additional information in particular cases.

The determination of the contents of amines in steps d and f is preferably carried out by determining the ion mobility spectrum of the vapors, though it could be carried out by other, known analysis methods, so that the reference to ion mobility spectra should not be construed as limiting. The vapors collected at room temperature will contain the most volatile compounds, the contents of which will therefore be determined from said ion mobility spectra. Heating the sample thereafter will increase the vapor pressure of the less volatile compounds, driving them from the sample, and causing them to enter the gas phase. The resulting vapors will be rich in said less volatile compounds, the contents of which will therefore be determined from the ion mobility spectra of the vapors resulting from the heating.

Steps d and f of the process are preferably carried out by carrying the gas phase evolved at room temperature, and then the gas phase originating from the heating, to a detector or a measuring device for analyzing them, preferably by ion mobility spectrometry (IMS).

Among the volatile amines emanating from the sample at room temperature, trimethylamine (TMA) is an important component when the samples are body fluids collected for diagnostic purposes. Semi-volatile amines are putrescine and cadaverine. This invention enhances by a large factor the signal from said semi-volatile amines and the ratio of said signal to that pertaining to TMA.

Room temperature (RT) is understood herein to be from 20° C. to 30° C. The heating is preferably such as to bring the sample to a temperature from 50° C. to 100° C., and is carried out by any suitable means, such as electrical heating elements, microwave heaters, convection heaters, radiation emitters such as e.g. infrared heaters, and so on. Another possible way of heating the sample is to place it into a water-tight container and immerse the container in hot water (e.g. 94-95° C.). When the contents of amines is determined through the mobility spectra, the durations of stages d and f of the treatment are such as to permit to obtain said mobility spectra, viz. they are in the order of seconds, generally from 10 to 60 seconds.

As has been said, the analysis of the vapors obtained from the emanation of the sample at room temperature, which may be called "first stage vapors", is preferably carried out by IMS. A suitable IMS apparatus is, for instance, prototype IMS (PT-IMS), made by Rotem Industries Ltd., Israel. The same means are suitable for analyzing the vapors obtained from the emanation of the samples during heating, which may be called "second stage vapors".

BRIEF DESCRIPTION OF THE DRAWINGS

The present invention can be more fully appreciated with reference to the following detailed description, which, in turn, refers to the drawings, in which:

FIG. 6 is a graphical representation showing the mobility spectra such as those of FIG. 5, but obtained by adding KOH to the mixture;

FIG. 7 is a graphical representation showing the mobility spectra such as those of FIGS. 5 and 6, but obtained after adding firstly nitric acid and then KOH;

FIG. 8 is a graphical representation showing the mobility spectra, similar to those of FIGS. 5, 6 and 7, but of a sample of vaginal fluid with a cotton Q-tip;

FIG. 9 is a graphical representation showing the mobility spectra, similar to those of FIGS. 5, 6 and 7, but of another sample of vaginal fluid with a cotton Q-tip;

FIG. 10 is a graphical representation showing the mobility spectra, similar to those of FIGS. 5, 6 and 7, but of another sample of vaginal fluid with a cotton Q-tip;

FIG. 11 is a graphical representation showing the mobility spectra, similar to those of FIGS. 5, 6 and 7, but of a sample of a piece of chicken collected after one day in a refrigerator.

FIG. 12 is a graphical representation showing the mobility spectra, similar to those of FIGS. 5, 6 and 7, but of another sample of a piece of chicken collected after one day in a refrigerator.

FIG. 13 is a graphical representation showing the mobility spectra, similar to those of FIGS. 5, 6 and 7, but of another sample of a piece of chicken collected after one day in a refrigerator.

DETAILED DESCRIPTION

Figure 2:
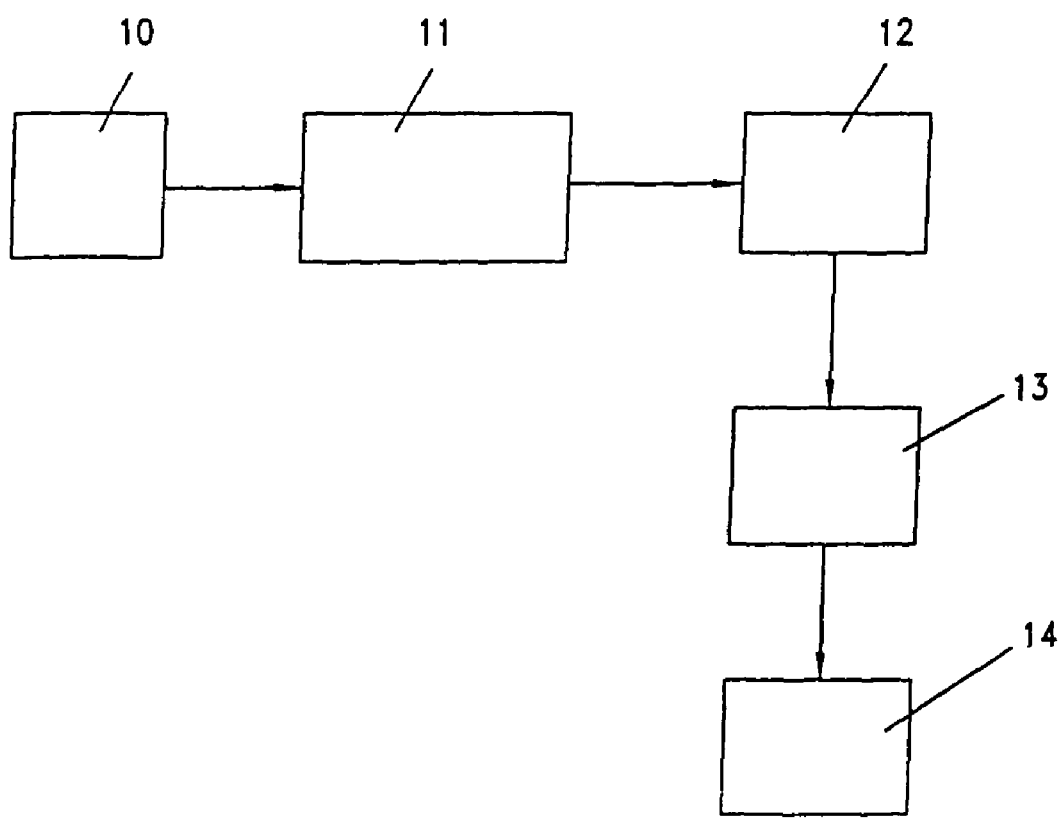
FIG. 2 is a schematic block diagram of the apparatus of the present invention.

A block diagram of an apparatus for carrying out the invention is given in FIG. 2. In said figure, numeral 10 indicates a chemical reaction chamber. 11 is an ion mobility measurement device, e.g. an IMS. 12 is an analog-to-digital converter for the acquisition, from the ion mobility measurements, of the data that are considered relevant. 13 is a processor for processing the acquired data according to a predetermined program. 14 is an output device that shows the presence or absence or suspicion of presence of predetermined pathological conditions.

The following flowsheet of operations illustrates an embodiment of the invention:
1) Insert sample into chemical chamber
2) Add chemical reagent(s) to enhance emanation of volatile compounds
3) Transport vapors into ionization region of the IMS
4) Ionize vapors directly and through chemical gas-phase ion-molecule reactions
5) Detect ions, measure their mobility and quantify them.
6) Acquire data or spectra
7) Process data and compare to stored data (library, spectra or tables).
8) Output the result: Presence/absence of condition or suspicion that the condition exists.

Figure 3:
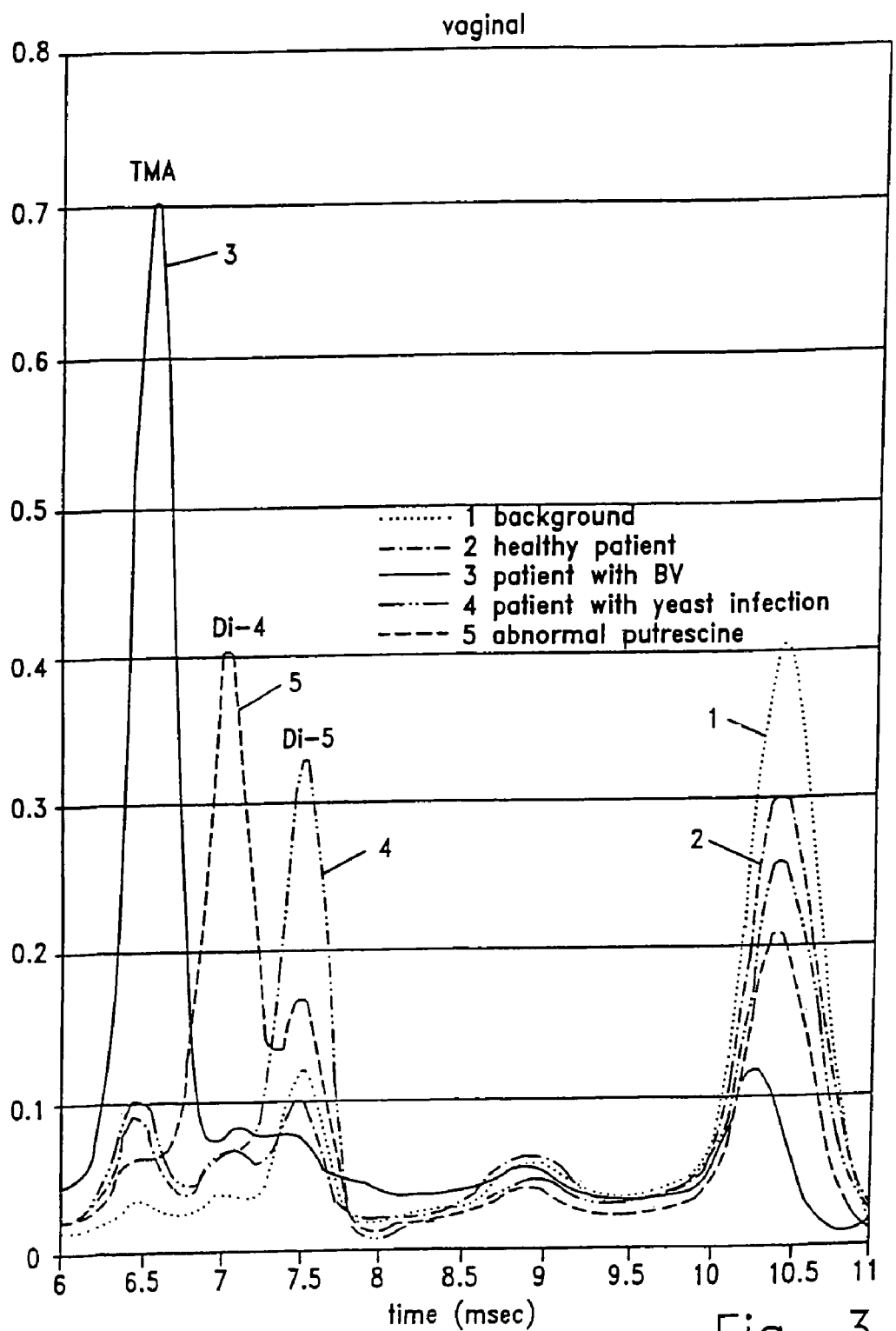
FIG. 3 is a graphical representation showing the peaks indicating the evolution of amines vapors from a number of vaginal fluid samples.

FIG. 3 comprises a diagram, showing various curves, relative to different vaginal fluid samples. Vapors emanating from each sample were ionized, and the amounts of ions from different amines, particularly TMA, putrescine and cadaverine were measured. The vapors emanate at the same time, but the ions formed from the different compounds have different mobilities, so that when they are measured and reported as in FIG. 3 as a function of time, the peaks of the diagram indicate the amounts of the different amines that are recognized from the time at which they give a signal. The peaks relating to TMA, putrescine and cadaverine are indicated in FIG. 3 as TMA, Di-4 and Di-5 respectively. The curves relative to the various samples are identified by numbers at the side of FIG. 3 and it is seen that sample No. 3 has an abnormally high content of TMA, indicating bacterial vaginosis. Curve 1 is the background spectrum, obtained when a clean Q-tip is inserted into the chemical reaction chamber and 300 µL of 8N KOH solution are added. Curve 2 is the mobility spectrum obtained from a vaginal fluid sample of a healthy woman with no vaginal disorder. Curve 3 was obtained from a vaginal fluid sample of a woman diagnosed as having a vaginal infection identified as bacterial vaginosis (BV) according to the Amsel test. Curve 4 was obtained from a vaginal fluid sample of a woman diagnosed as having a vaginal yeast infection. The abnormally high level of putrescine seen in Curve 5 is indicative of an unspecified vaginal disorder or infection.

Figure 4:
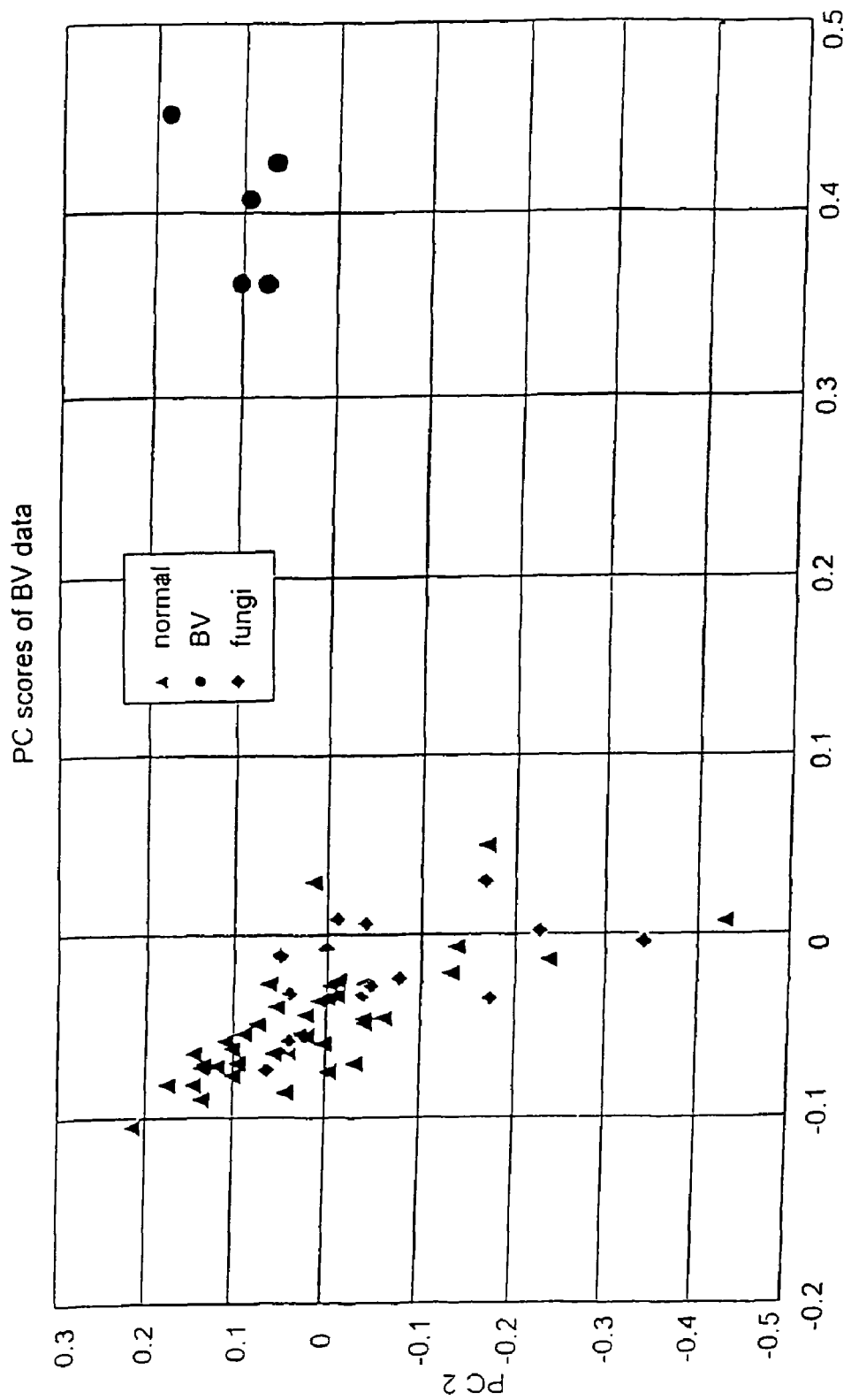
FIG. 4 is a graphical representation showing the Principal Component (PC) analysis of a number of vaginal fluid samples analyzed for Bacterial Vaginosis (BV)

FIG. 4 represents the scores of each mobility spectrum on the first two principal components (PC). The first principal component (the abscissa) represents the content of trimethylamine (TMA) in the mobility spectrum. The second principal component (the ordinate axis) represents the content of the diamines (putrescine and cadaverine). The cluster of points in the upper right hand corner (circles) is obtained from vaginal samples of women with bacterial vaginosis. The diamond shaped data points were obtained from vaginal samples diagnosed by the gynecologist as suffering from some vaginal disorder (yeast, trichomonas or elevated pH levels). The triangles represent vaginal samples taken from women with no reported or observed vaginal disorder.

The invention can also be applied, as set forth hereinbefore, for checking the freshness of meat.

The following examples are illustrative and in no way should be construed as limiting the invention. A first example of the invention will be given with reference to a diagnostic response relative to cancer.

Example 1

In this example, the Ion Mobility Spectrometers (IMS) used were PhemtoChem-100 made by PCP Inc., West Palm Beach, Fla., USA and PTIMS made by Rotem Industries, Mishor Yamin, Israel. However, any properly equipped IMS made be used to obtain such spectra. The first and second elaborators, in this example, are combined into a single computer which comprises a permanent memory, a buffer memory, a CPU, a screen, a BUS providing the necessary electrical connections, power means, a keyboard, and all obvious accessories. Generally, IMS may display the biogenic amine spectrum or display their results in the form of a histogram series of bars or as a table of compounds. In any case, the IMS transmits to the buffer memory the amine spectrum. The operator has chosen, by means of the keyboard, the type of response which he wants. In this case, he has chosen a response which relates to the presence of a cancer. The CPU is programmed to draw from the buffer memory the data of the amine spectrum and calculate from them the measured parameters which are relevant to the diagnosis of cancer, according to a program which is stored in the permanent memory and which the CPU has drawn from said memory once the operator's choice has been made. The CPU also draws from the permanent memory the comparative parameters and carries out the necessary comparison to draw the response required.

Figure 1:
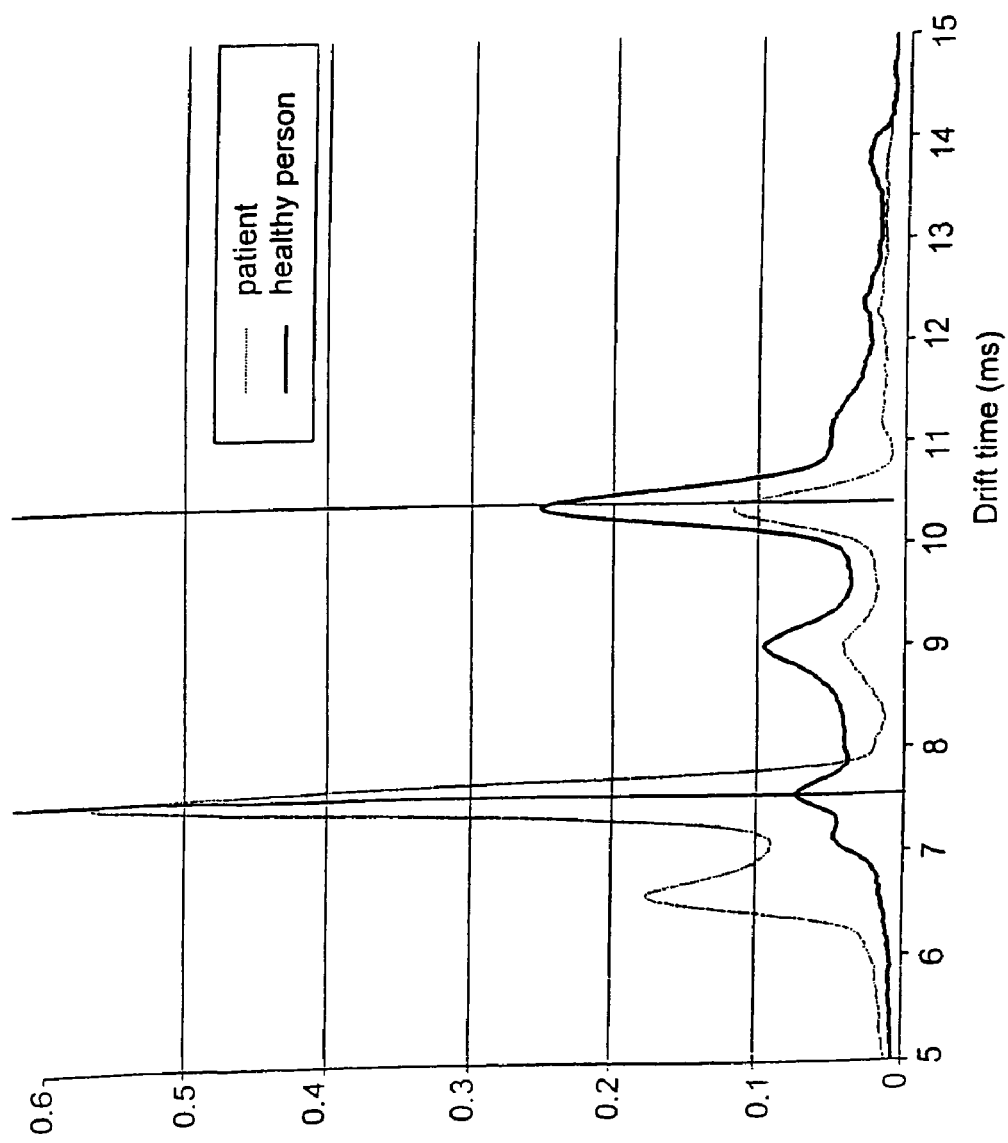
FIG. 1 is a graphical representation of the biogenic amine spectrum of the urine of a cancer patient and the comparable spectrum of a healthy subject.

FIG. 1 shows two curves relating to a healthy person and to a cancer patient respectively, as indicated in the drawing. The abscissa is the time at which the various amines appear and the ordinate is their amount, and since the various amines appear at different time, each curve constitutes an amine spectrum. The different peaks that appear permit to diagnose the presence of a disease, in this case cancer.

Example 2

Figure 5:
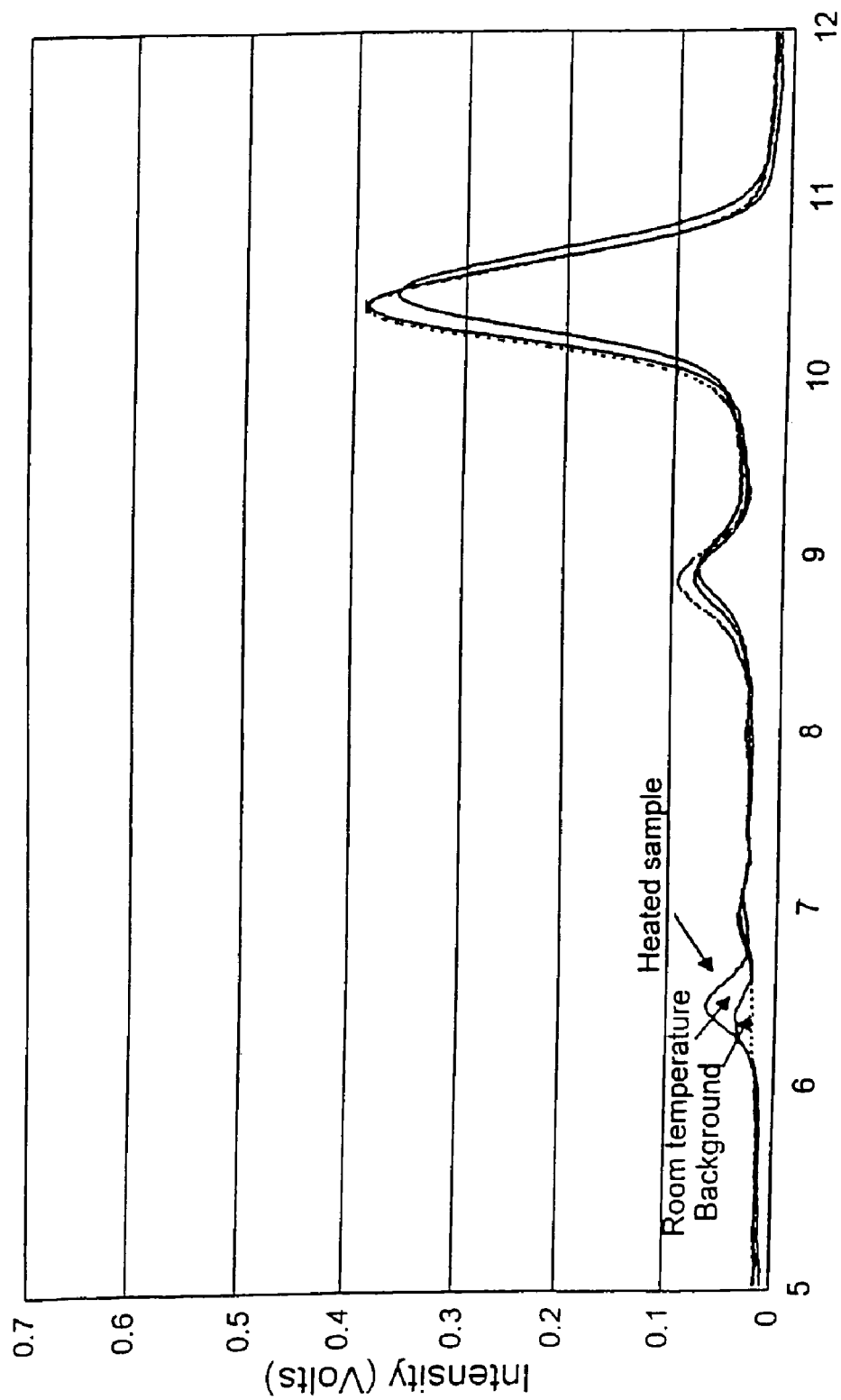
FIG. 5 is a graphical representation showing the mobility spectra of a sample of 0.1 mL of a mixture containing putrescine, cadaverine, TMA (25:50:5 mmoles), obtained without the addition of a reagent; two solid lines indicating the spectra obtained at room temperature and under heating, while a broken line indicates the background mobility spectrum of the instrument used.
Figure 6:
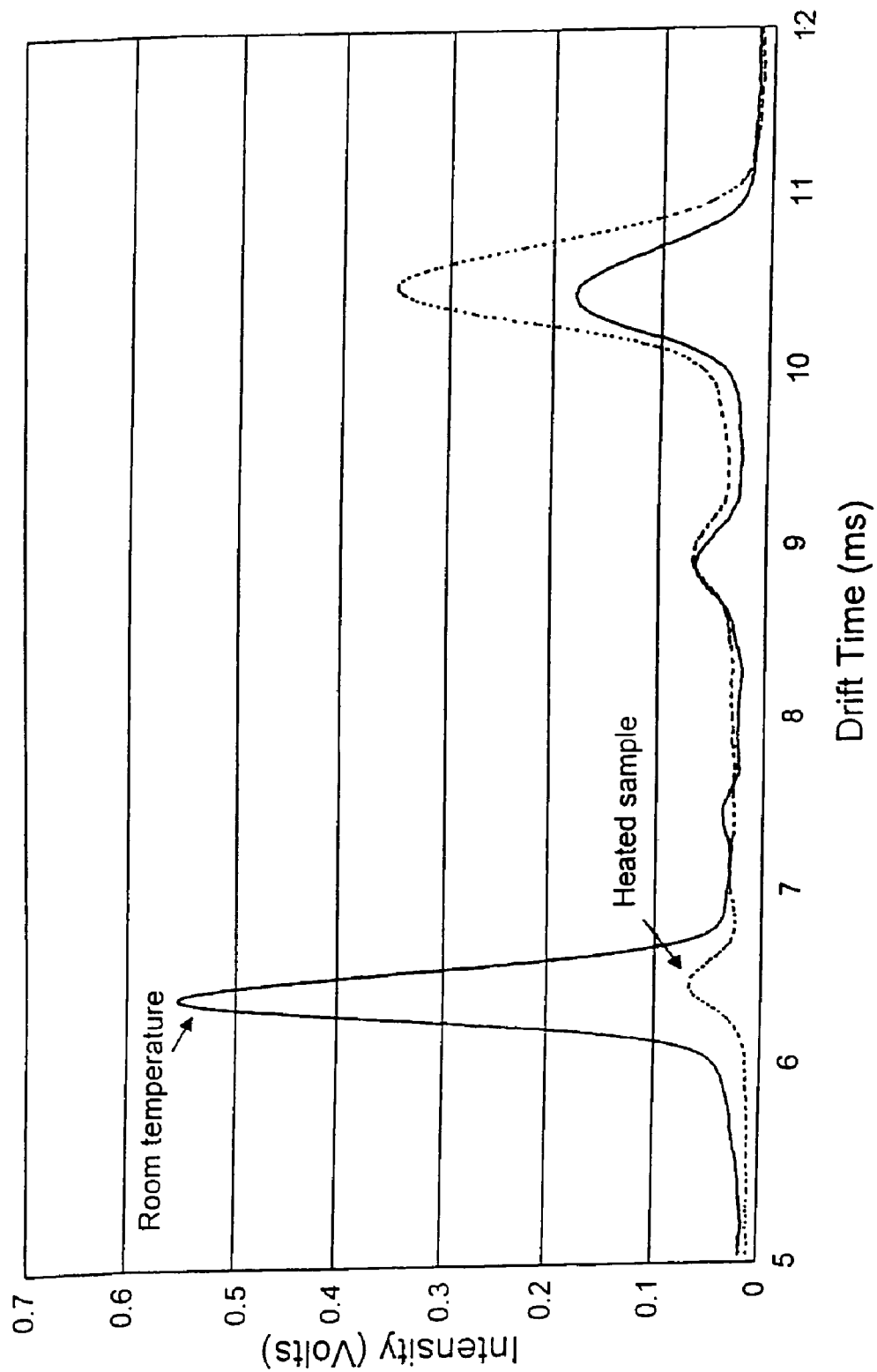
FIGS. 6 to 13 are graphical representations of each of two mobility spectra: one obtained at room temperature, shown in solid lines, and one obtained during heating which raised the temperature of the sample to about 60° C., shown on broken lines; the abscissas indicating the time in milliseconds (msec) and the ordinates indicating the signal intensity in volts, which is proportional to the amount of each amine emanated, under the conditions of the various experiments.
Figure 7:
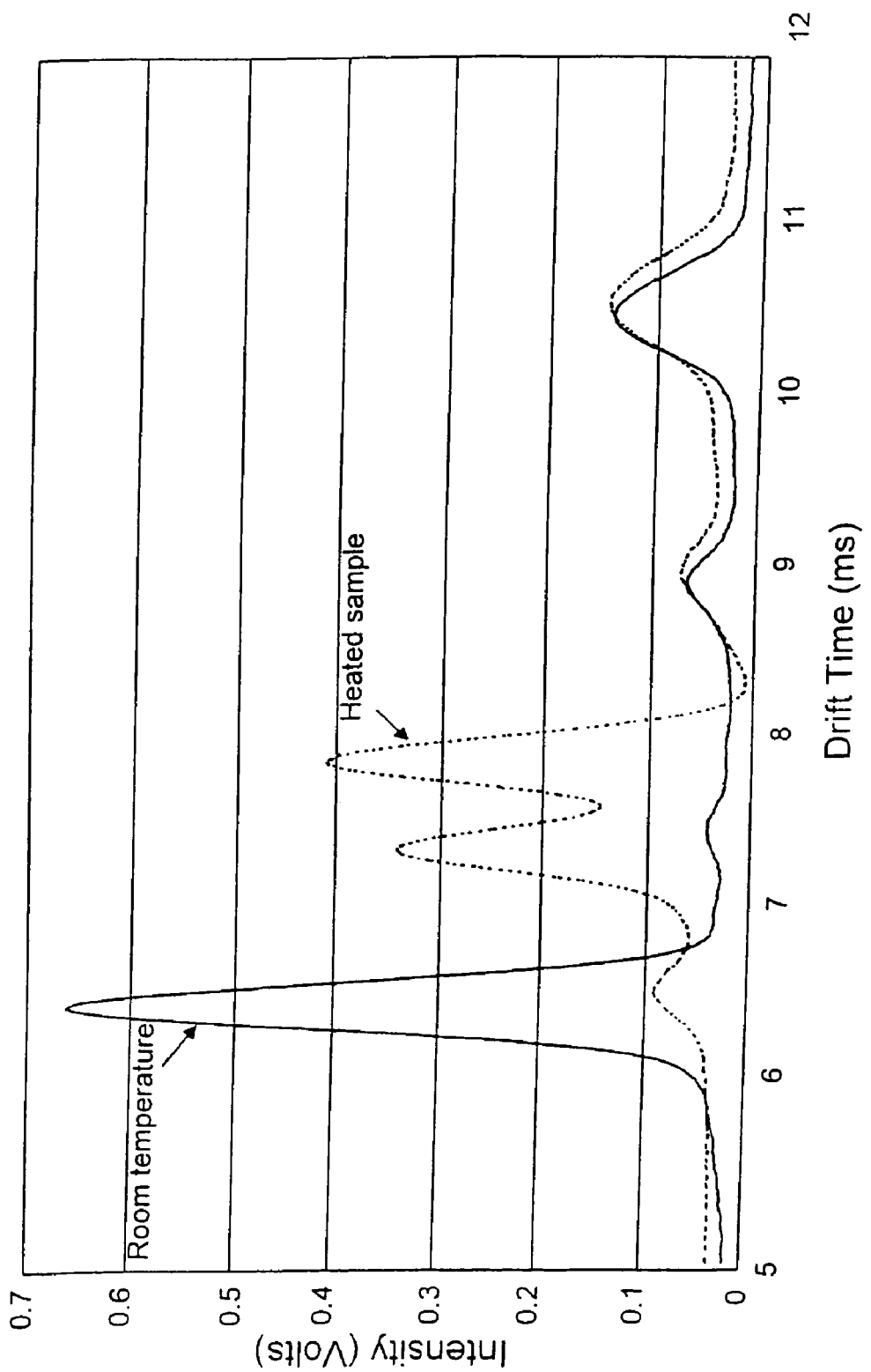

A sample of 0.1 mL of a mixture ("cocktail") containing 25:50:5 mmoles putrescine:cadaverine:TMA (220:510:29.5 ng (nanograms) in sample) was analyzed by IMS.
a) FIG. 5—Without reagents at room temperature (23° C.) and during immersion in hot water (94° C.). As clearly indicated in the drawing, one curve was obtained at room temperature and another curve was obtained when the sample was immersed in hot water. Further, the broken line shows the background mobility spectrum of the instrument. The biogenic amines were not identified.
b) FIG. 6—After addition of 0.3 mL of 4N KOH solution at room temperature (23° C.) and during immersion in hot water (94° C.). The curve in solid line was obtained at room temperature; the curve in dashed line was obtained when the sample was immersed in hot water. A large TMA peak was observed at room temperature, but once the sample was heated, most of the TMA was boiled off. The other biogenic amines were not identified.
c) FIG. 7—After addition of 1 drop 10% $HNO_3$ followed by the addition of 0.3 mL of 4N KOH solution at room temperature (23° C.) and during immersion in hot water (94° C.). The curve in solid line was obtained at room temperature; the curve in dashed line was obtained when the sample was immersed in hot water. The TMA peak is similar in intensity to that in FIG. 6, but heating results in large peaks for cadaverine and putrescine, which could not be observed previously.

Example 3

Figure 8:
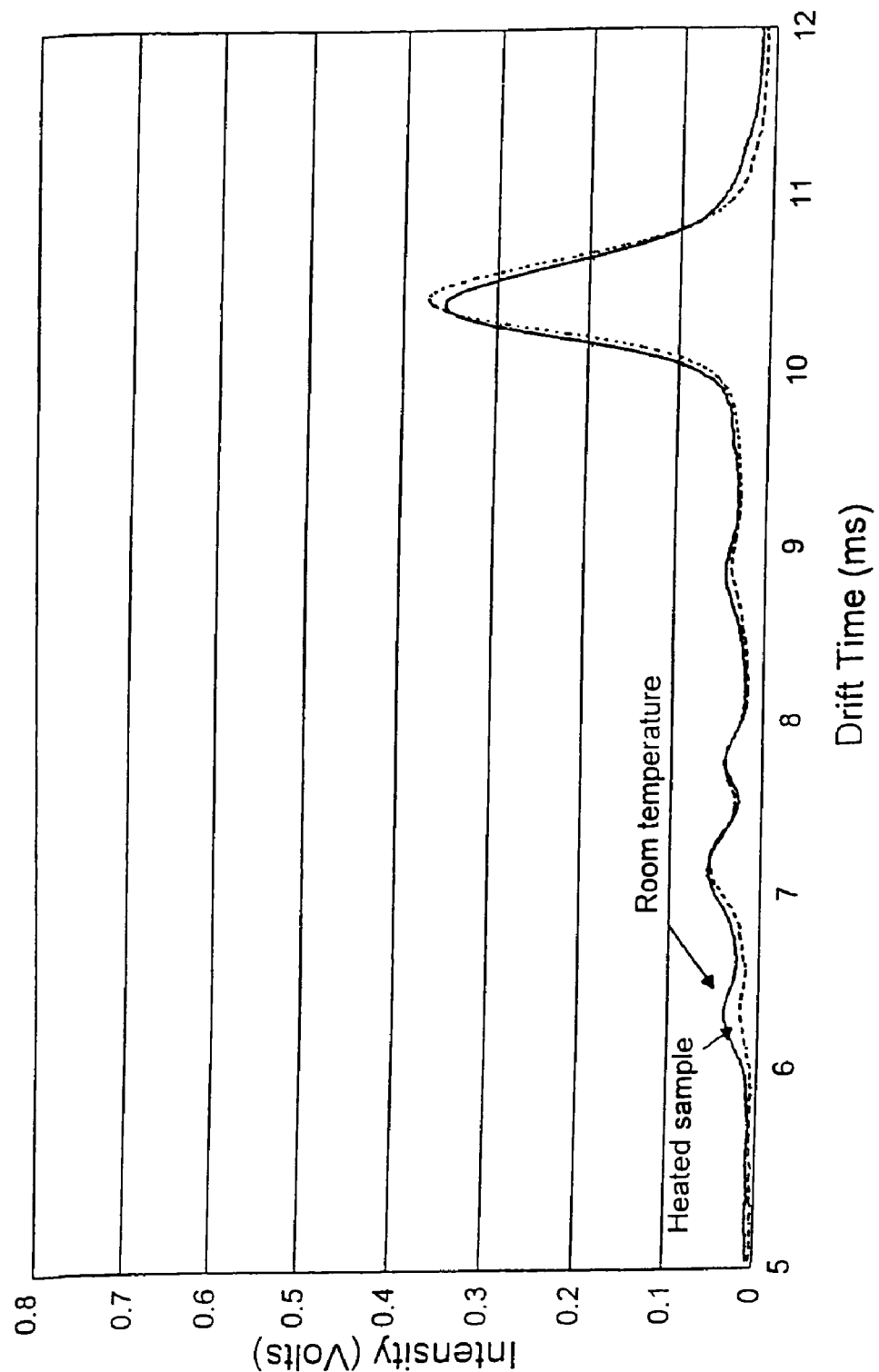
Figure 9:
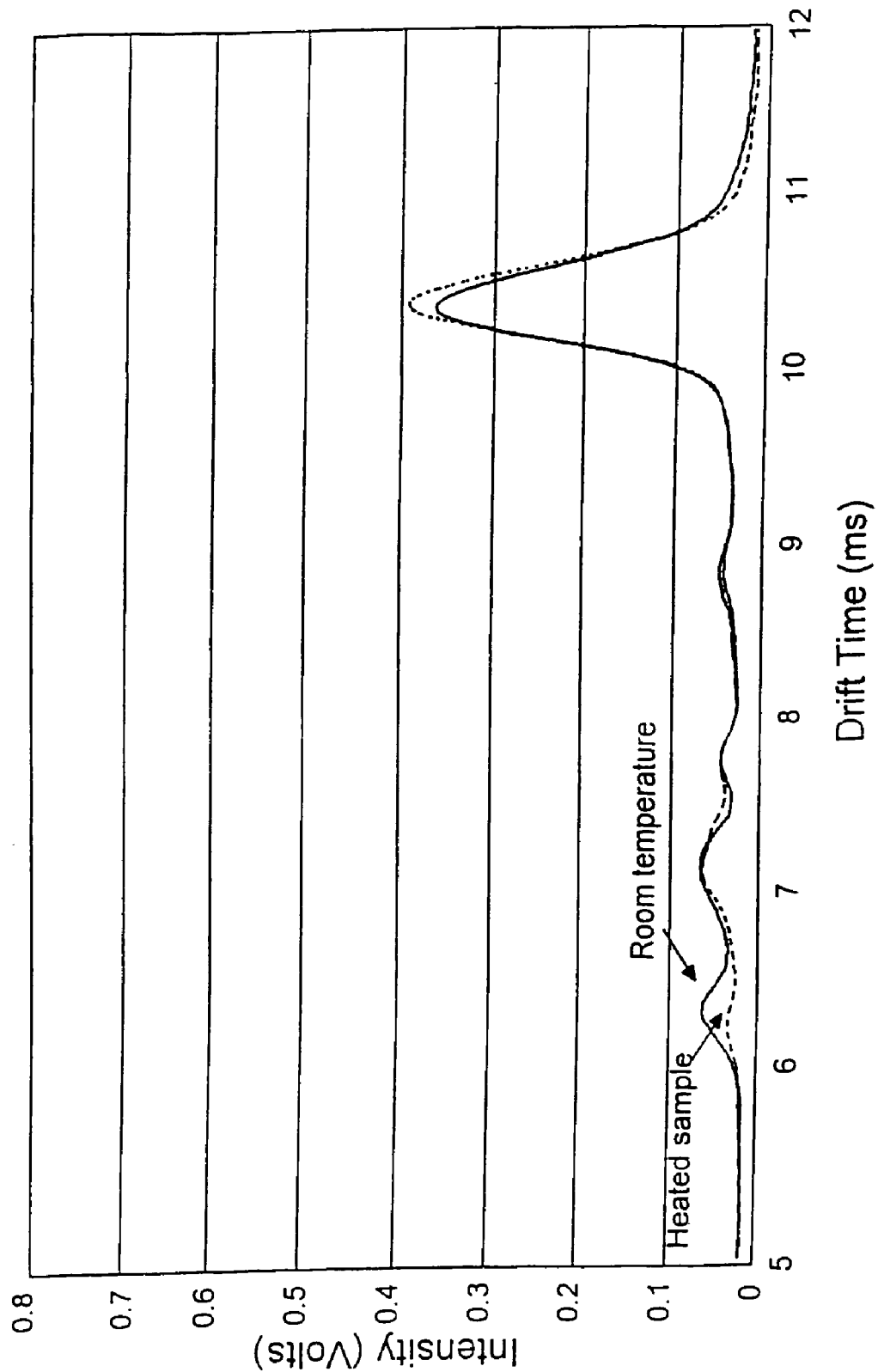
Figure 10:
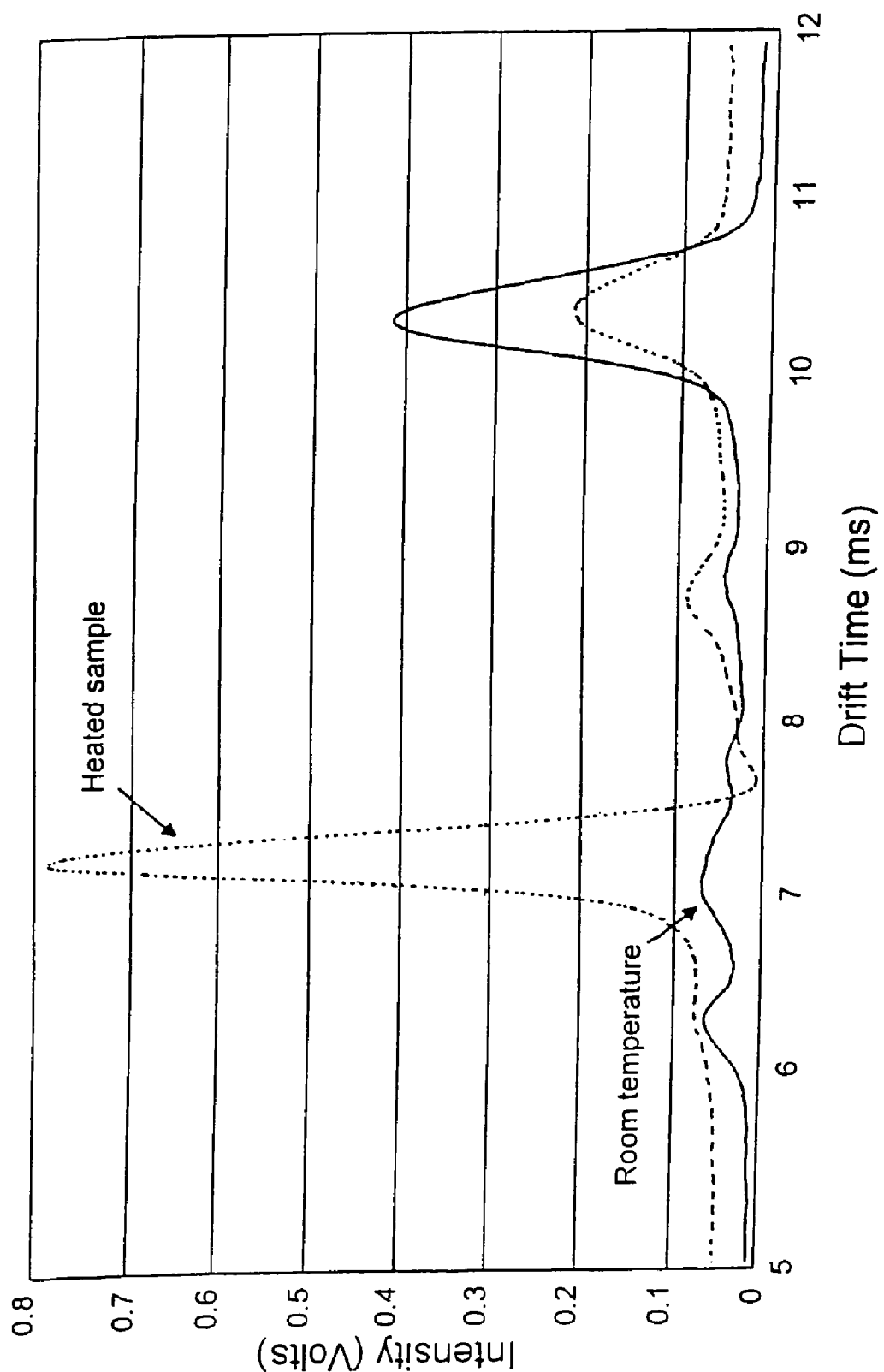

A 0.1 mL sample, collected by rinsing the vagina with 2 mL of saline solution from a female patient with a vaginal infection, was analyzed by IMS:
a) FIG. 8—Without reagents at room temperature (23° C.) and during immersion in hot water (94° C.). The curve in solid line was obtained at room temperature; the curve in dashed line was obtained when the sample was immersed in hot water. Biogenic amines were not identified.
b) FIG. 9—After addition of 0.3 mL of 4N KOH solution at room temperature (23° C.) and during immersion in hot water (94° C.). The curve in solid line was obtained at room temperature; the curve in dashed line was obtained when the sample was immersed in hot water. Biogenic amines were not identified.
c) FIG. 10—After addition of 1 drop 10% $HNO_3$ followed by the addition of 0.3 mL of 4N KOH solution at room temperature (23° C.) and during immersion in hot water (94° C.). The curve in solid line was obtained at room temperature; the curve in dashed line was obtained when the sample was immersed in hot water. The presence of putrescine was clearly observed in the mobility spectrum of the heated sample.

Example 4

Figure 11:
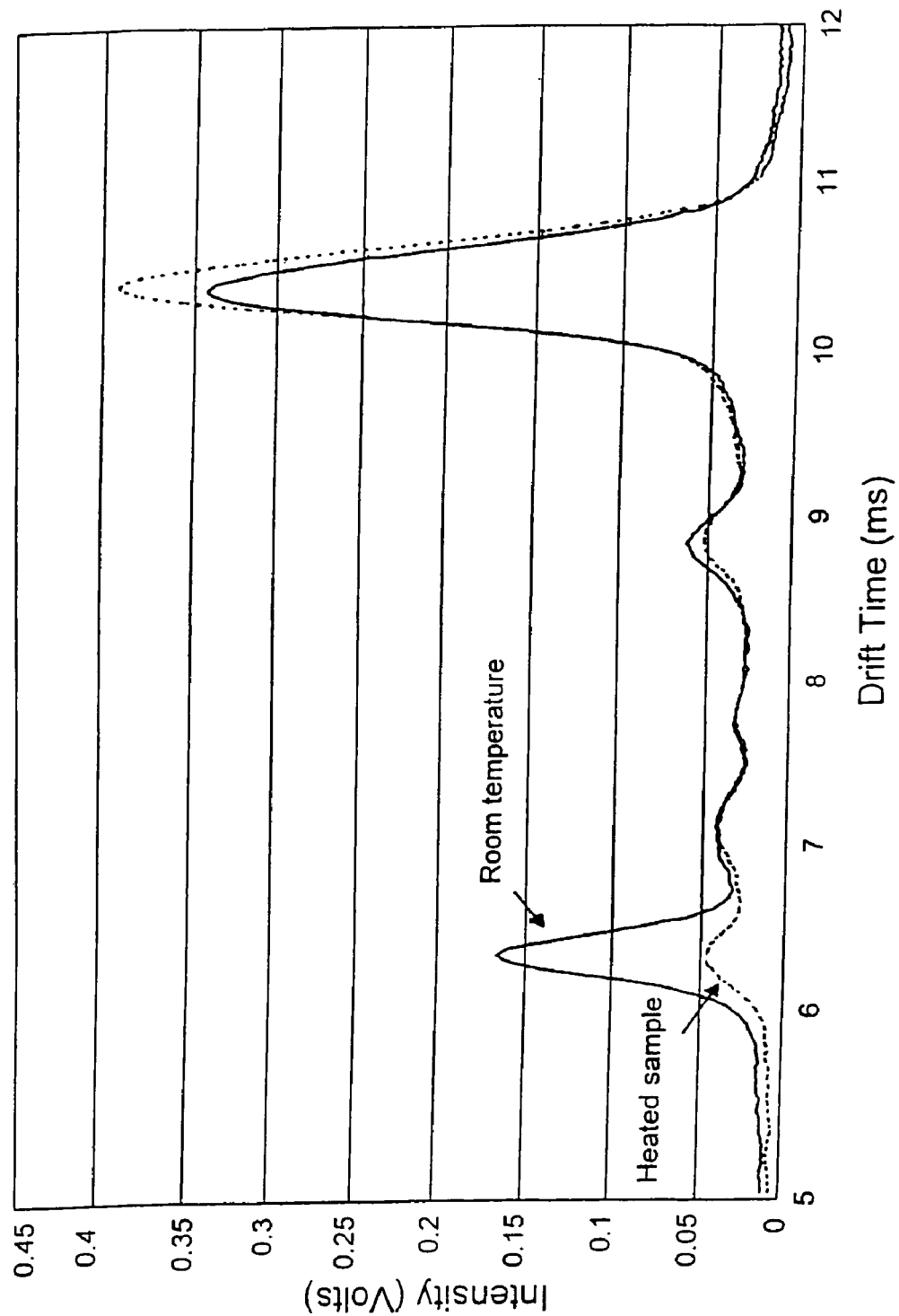
Figure 12:
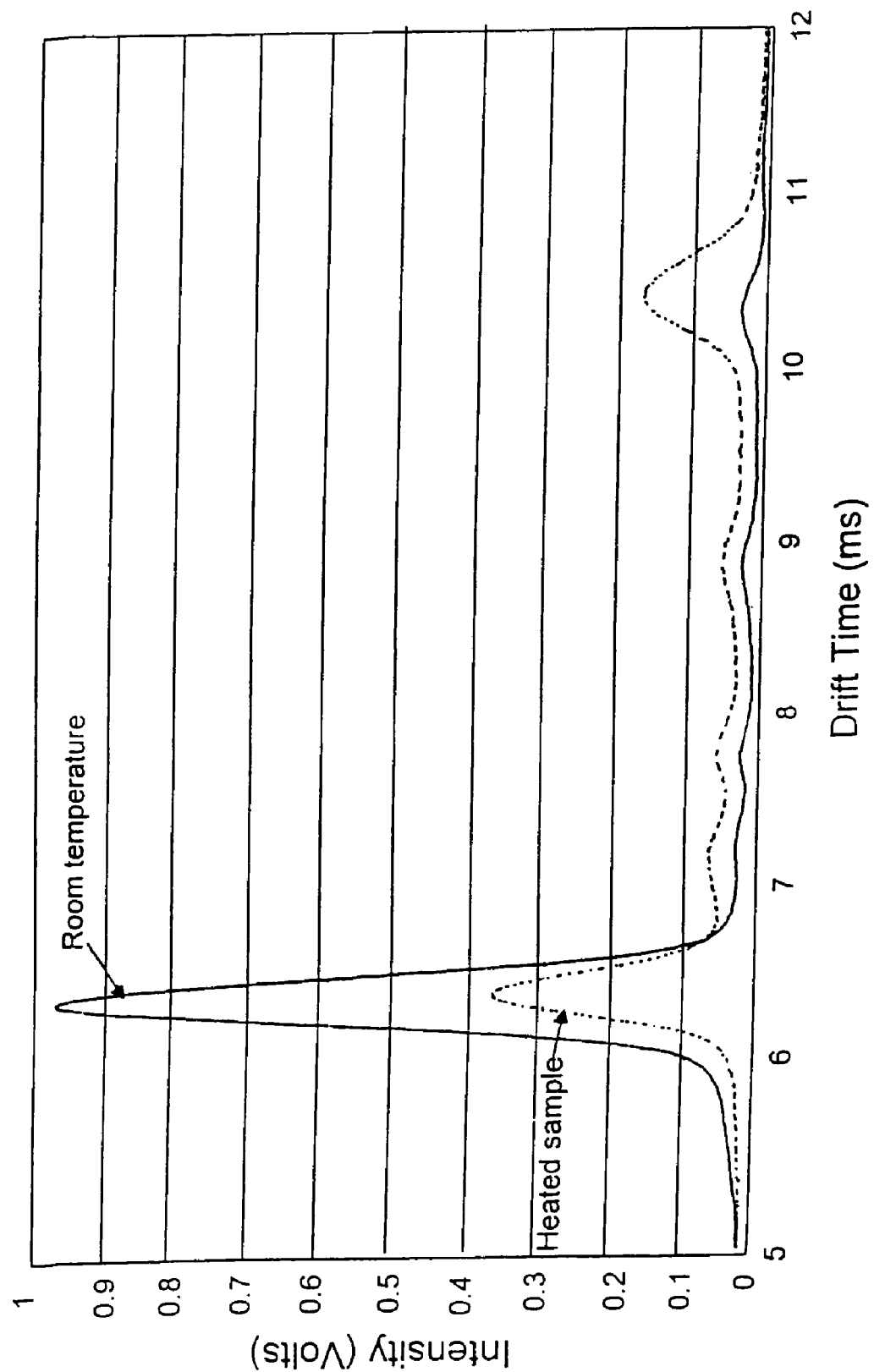
Figure 13:
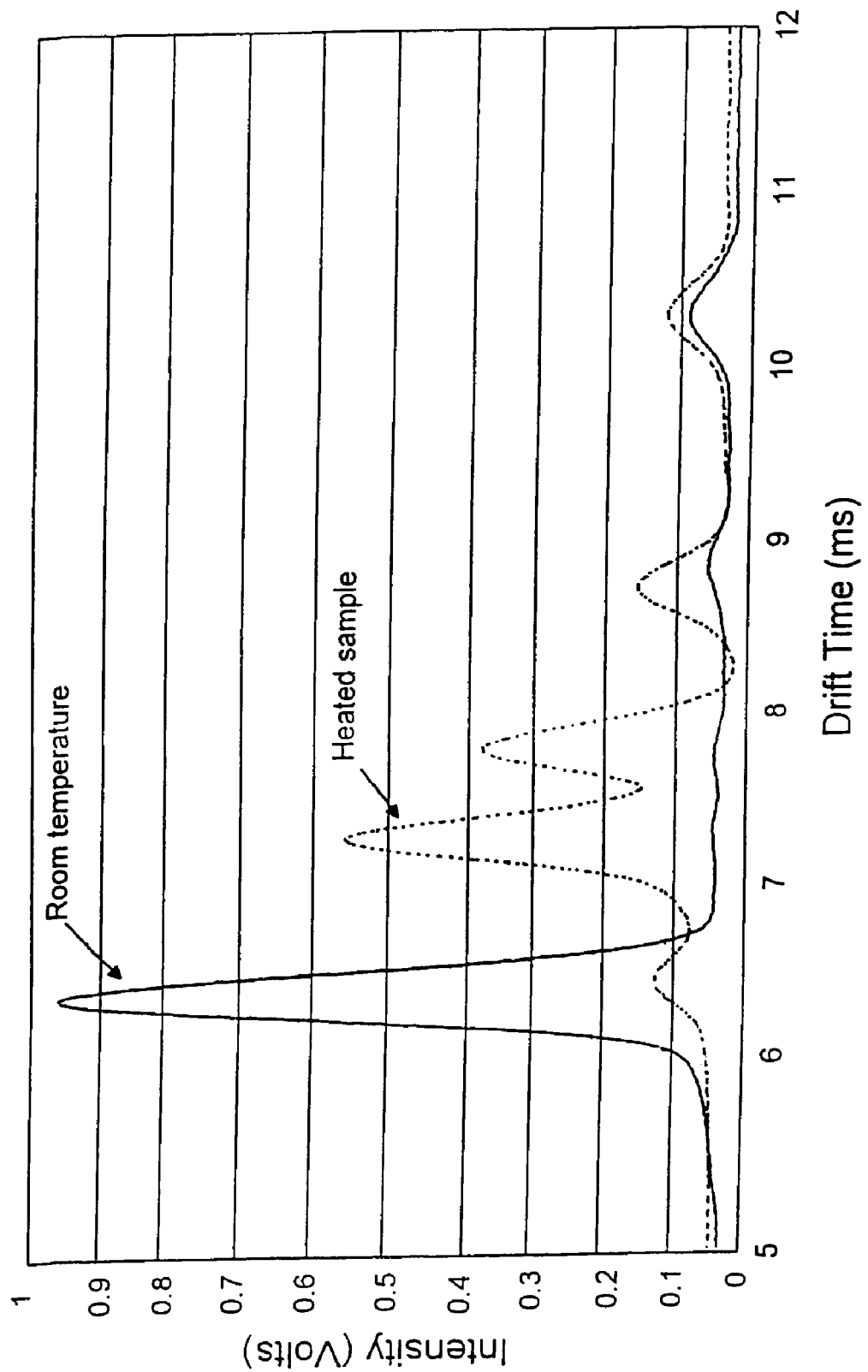

A sample collected from a piece of chicken after one day in a refrigerator, was analyzed by IMS:
a) FIG. 11—Without reagents at room temperature (23° C.) and during immersion in hot water (94° C.). The curve in solid line was obtained at room temperature; the curve in dashed line was obtained when the sample was immersed in hot water. A small TMA peak was observed, but other biogenic amines were not identified.
b) FIG. 12—After addition of 0.3 mL of 4N KOH solution at room temperature (23° C.) and during immersion in hot water (94° C.).). The curve in solid line was obtained at room temperature; the curve in dashed line was obtained when the sample was immersed in hot water. The TMA peak was larger at RT, but other biogenic amines were not identified.
c) FIG. 13—After addition of 1 drop 10% $HNO_3$ followed by the addition of 0.3 mL of 4N KOH solution at room temperature (23° C.) and during immersion in hot water (94° C.). The curve in solid line was obtained at room temperature; the curve in dashed line was obtained when the sample was immersed in hot water. The presence of putrescine and cadaverine were clearly observed in the mobility spectrum of the heated sample, while the TMA peak was large at RT.

The same instrument is used for all the measurements and therefore the background spectrum shown in FIG. 5 is not repeated in the following figures. The instrument used was a prototype ion mobility spectrometer (PT-IMS) made by Rotem Industries Ltd., Israel.

In conclusion, the signal intensities in an IMS derived from biogenic amines without an alkali solution are negligibly small. Addition of an alkali solution leads to enhanced emanation of volatile amines, such as trimethylamine, while less volatile amines are hardly seen in the mobility spectrum. Immersion in hot water (94° C.) results in boiling off the volatile compounds, while the less volatile ones are still barely observed. However, pretreatment with acid, followed by the alkaline solution, leads to emanation of volatile amines at room temperature, and of the less volatile amines when the example is immersed in hot water.

The overall effect of the process of the invention is an enhancement of emanation of all amines by addition of an alkaline solution (a fact well known), but also a selective enhancement of emanation of less volatile amines by combining acid pretreatment with heat. Thus, the presence of putrescine and cadaverine can only readily be noticed once both pretreatment with acidification and heat are applied to the sample.

In the drawings, the abscissa indicates time in milliseconds and the ordinate indicates the amount of each amine emanated, under the conditions of the various experiments, as units of volts. In FIG. 5, a broken line indicates the background mobility spectrum of the instrument used. The same instrument is used for all the measurements and therefore said background spectrum is not repeated in the following figures. The instrument used was the aforesaid PT-IMS.

While embodiments of the invention have been described by way of illustration, it should be understood that the invention may be carried out with many modifications, variations and adaptations, without exceeding the scope of the claims.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method for the evaluation of a biological sample, based on the amounts of biogenic amines, which comprises:
    a) successively adding, in any order, a strong acid and a strong base to the sample comprising or derived from a vaginal discharge or fluid to effect a basic pH;
    b) collecting a first vapor emanating from the sample at room temperature and determining a first amine content of the first vapor;
    c) heating the sample;
    d) collecting a second vapor emanating from the sample upon heating and determining a second amine content of the second vapor; and
    e) performing a first comparison between the first determined amine content and a first predetermined amine content, performing a second comparison between the second determined amine content and a second predetermined amine content, and evaluating the sample based upon the first and second comparisons.

2. The method according to claim 1, wherein the sample is derived from a human body.

3. The method according to claim 1, further comprising the steps of ionizing one or both of the first and second vapors and measuring the presence of amine compounds in the ionized vapor by the appearance of ions derived from said compounds in an ion mobility measurement.

4. The method according to claim 1, further comprising enhancing emanation of amine vapors by addition of reagents that transform the amine compounds to more volatile forms.

5. The method according to claim 4, wherein the reagents are selected from the group consisting of alkaline solutions or ammonia.

6. The method according to claim 1, wherein the step of determining the amine content of the second vapor comprises determining the content of putrescine and/or cadaverine in the second vapor.

7. The method according to claim 1, wherein the step of determining the amine content of the first vapor comprises determining the content of trimethylamine.

8. The method according to claim 1, wherein the vapors are analyzed by ion mobility spectrometry.

9. The method according to claim 1, wherein the base is an alkaline solution and the acid is a mineral acid solution.

10. The method according to claim 1, wherein the heating is carried out so as to bring the sample to a temperature from 50° C. to 100° C.

11. The method according to claim 1, wherein the heating is carried out by immersing the sample in hot water.

12. The method according to claim 1, wherein the heating is carried out by a means selected from the group consisting of electrical heaters, microwave heaters, convection heaters and infrared heaters.

13. The method according to claim 1, wherein the sample is derived from a vaginal fluid.

14. The method according to claim 1, wherein the evaluation is for the diagnosis of a vaginal disease.

15. A method for the evaluation of a biological sample, based on the amounts of biogenic amines, which comprises:
   a) successively adding, in any order, an acid and a base to the sample comprising or derived from a vaginal discharge or fluid to effect a pH of about 14;
   b) collecting a first vapor emanating from the sample at room temperature and determining a first amine content of the first vapor;
   c) heating the sample;
   d) collecting a second vapor emanating from the sample upon heating and determining a second amine content of the second vapor; and
   e) performing a first comparison between the first determined amine content and a first predetermined amine content, performing a second comparison between the second determined amine content and a second predetermined amine content, and evaluating the sample based upon the first and second comparisons.

16. The method according to claim 15, further comprising the steps of ionizing one or both of the first and second vapors and measuring the presence of amine compounds in the ionized vapor by the appearance of ions derived from said compounds in an ion mobility measurement.

17. The method according to claim 15, wherein the step of determining the amine content of the second vapor comprises determining the content of putrescine and/or cadaverine in the second vapor.

18. The method according to claim 15, wherein the step of determining the amine content of the first vapor comprises determining the content of trimethylamine.

19. The method according to claim 15, wherein the heating is carried out so as to bring the sample to a temperature from 50° C. to 100° C.

20. A method for the evaluation of a biological sample, based on the amounts of biogenic amines, which comprises:
   a) adding a base to the sample comprising or derived from a vaginal discharge or fluid to effect a pH of about 14;
   b) collecting a first vapor emanating from the sample at room temperature and determining a first amine content of the first vapor;
   c) heating the sample;
   d) collecting a second vapor emanating from the sample upon heating and determining a second amine content of the second vapor; and
   e) performing a first comparison between the first determined amine content and a first predetermined amine content, performing a second comparison between the second determined amine content and a second predetermined amine content, and evaluating the sample based upon the first and second comparisons.

21. The method according to claim 20, further comprising the steps of ionizing one or both of the first and second vapors and measuring the presence of amine compounds in the ionized vapor by the appearance of ions derived from said compounds in an ion mobility measurement.

22. The method according to claim 20, wherein the step of determining the amine content of the second vapor comprises determining the content of putrescine and/or cadaverine in the second vapor.

23. The method according to claim 20, wherein the step of determining the amine content of the first vapor comprises determining the content of trimethylamine.

24. The method according to claim 20, wherein the heating is carried out so as to bring the sample to a temperature from 50° C. to 100° C.

* * * * *